US012693362B2

(12) United States Patent
Edelman

(10) Patent No.: US 12,693,362 B2
(45) Date of Patent: Jul. 28, 2026

(54) SYSTEM AND METHOD FOR T₁ RELAXATION ENHANCED STEADY-STATE MRI

(71) Applicant: NORTHSHORE UNIVERSITY HEALTHSYSTEM, Evanston, IL (US)

(72) Inventor: Robert R. Edelman, Highland Park, IL (US)

(73) Assignee: Endeavor Health Clinical Operations, Evanston, IL (US)

( * ) Notice: Subject to any disclaimer, the term of this patent is extended or adjusted under 35 U.S.C. 154(b) by 172 days.

(21) Appl. No.: 18/654,521

(22) Filed: May 3, 2024

(65) Prior Publication Data

US 2024/0280658 A1 Aug. 22, 2024

Related U.S. Application Data

(63) Continuation-in-part of application No. 17/911,809, filed as application No. PCT/US2021/021895 on Mar. 11, 2021.

(Continued)

(51) Int. Cl.
*G01R 33/56* (2006.01)
*A61B 5/00* (2006.01)
(Continued)

(52) U.S. Cl.
CPC ..... *G01R 33/5602* (2013.01); *G01R 33/5601* (2013.01); *G01R 33/5607* (2013.01);
(Continued)

(58) Field of Classification Search
CPC ........... G01R 33/5602; G01R 33/5601; G01R 33/5608; G01R 33/5614; G01R 33/5607;
(Continued)

(56) References Cited

U.S. PATENT DOCUMENTS 10,145,920 B2 * 12/2018 Rehwald ........... G01R 33/5602
11,287,501 B1 3/2022 Tamada
(Continued)

FOREIGN PATENT DOCUMENTS

WO 2021/188355 A1 9/2021

OTHER PUBLICATIONS

Riederer SJ, Stinson EG, Weavers PT. Technical Aspects of Contrast-enhanced MR Angiography: Current Status and New Applications. Magn Reson Med Sci 2018; 17(1):3-12.
(Continued)

*Primary Examiner* — Rishi R Patel
(74) *Attorney, Agent, or Firm* — Quarles & Brady LLP

(57) ABSTRACT

A method for equilibrium phase contrast-enhanced magnetic resonance (MR) angiography using an extracellular MR contrast agent administered to a subject includes performing a balanced T₁ relaxation enhanced steady-state (bT₁RESS) pulse sequence to acquire MR data from a region of interest of the subject during an equilibrium phase of contrast enhancement after a first pass of the extracellular contrast agent through the region of interest. The bT₁RESS pulse sequence includes a T₁-weighted magnetization preparation including at least one contrast modifying (CM) radio frequency (RF) pulse, a single-shot balanced steady-state free precession (bSSFP) readout, and a time interval between the T₁-weighted magnetization preparation and the acquisition of a center of k-space. The time interval is determined based on a T₁ relaxation time of a contrast-enhanced blood pool and a flip angle of the at least one CM RF pulse. The method further includes generating an angiographic image of the region of interest.

22 Claims, 6 Drawing Sheets

Related U.S. Application Data

(60) Provisional application No. 62/991,181, filed on Mar. 18, 2020.

(51) Int. Cl.
| | |
|---|---|
| *A61B 5/055* | (2006.01) |
| *G01R 33/561* | (2006.01) |
| *G01R 33/563* | (2006.01) |

(52) U.S. Cl.
CPC ..... *G01R 33/5608* (2013.01); *G01R 33/5614* (2013.01); *G01R 33/5635* (2013.01); *A61B 5/0033* (2013.01); *A61B 5/055* (2013.01)

(58) Field of Classification Search
CPC .... G01R 33/5635; A61B 5/0033; A61B 5/055
See application file for complete search history.

(56) References Cited

U.S. PATENT DOCUMENTS

| | | | |
|---|---|---|---|
| 2010/0219829 A1 | 9/2010 | Rehwald et al. | |
| 2015/0123659 A1* | 5/2015 | Weingartner .......... | G01R 33/50 324/309 |
| 2018/0067184 A1 | 3/2018 | Weingartner et al. | |
| 2020/0256939 A1 | 8/2020 | Wang | |

OTHER PUBLICATIONS

Grist TM, Mistretta CA, Strother CM, Turski PA. Time-resolved angiography: Past, present, and future. Journal of magnetic resonance imaging : JMRI 2012;36(6):1273-1286.

Korosec FR, Frayne R, Grist TM, Mistretta CA. Time-resolved contrast-enhanced 3D MR angiography. Magn Reson Med 1996;36(3):345-351.

Groves EM, Bireley W, Dill K, Carroll TJ, Carr JC. Quantitative analysis of ECG-gated high-resolution contrast-enhanced MR angiography of the thoracic aorta. AJR American journal of roentgenology 2007; 188(2):522-528.

Patel AR, Salerno M, Kwong RY, Singh A, Heydari B, Kramer CM. Stress Cardiac Magnetic Resonance Myocardial Perfusion Imaging: JACC Review Topic of the Week. J Am Coll Cardiol 2021;78(16):1655-1668.

Breuer FA, Blaimer M, Mueller MF, et al. Controlled aliasing in volumetric parallel imaging (2D Caipirinha). Magn Reson Med 2006;55(3):549-556.

Lee VS, Martin DJ, Krinsky GA, Rofsky NM. Gadolinium-enhanced MR angiography: artifacts and pitfalls. AJR American journal of roentgenology 2000; 175(1):197-205.

Francois CJ, Tuite D, Deshpande V, Jerecic R, Weale P, Carr JC. Unenhanced MR angiography of the thoracic aorta: initial clinical evaluation. AJR American journal of roentgenology 2008; 190(4):902-906.

Correa Londono M, Trussardi N, Obmann VC, et al. Radial self-navigated native magnetic resonance angiography in comparison to navigator-gated contrast-enhanced MRA of the entire thoracic aorta in an aortic patient collective. Journal of cardiovascular magnetic resonance : official journal of the Society for Cardiovascular Magnetic Resonance 2021;23(1):94.

Potthast S, Mitsumori L, Stanescu LA, et al. Measuring aortic diameter with different MR techniques: comparison of three-dimensional (3D) navigated steady-state free-precession (SSFP), 3D contrast-enhanced magnetic resonance angiography (CE-MRA), 2D T2 black blood, and 2D cine SSFP. Journal of magnetic resonance imaging : JMRI 2010;31(1): 177-184.

von Knobelsdorff-Brenkenhoff F, Gruettner H, Trauzeddel RF, Greiser A, Schulz-Menger J. Comparison of native high-resolution 3D and contrast-enhanced MR angiography for assessing the thoracic aorta. Eur Heart J Cardiovasc Imaging 2014;15(6):651-658.

Haji-Valizadeh H, Collins JD, Aouad PJ, et al. Accelerated, free-breathing, noncontrast, electrocardiograph-triggered thoracic MR angiography with stack-of-stars k-space sampling and GRASP reconstruction. Magn Reson Med 2019;81(1):524-532.

Sebastia C, Sotomayor AD, Pano B, et al. Accuracy of unenhanced magnetic resonance angiography for the assessment of renal artery stenosis. European journal of radiology open 2016;3:200-206.

Kellman P, Zhang Q, Larson A, Simonetti O, McVeigh ER, Arai AE. Cardiac First-pass Perfusion MRI using 3d trueFISP Parallel Imaging using TSENSE. Proc Intl Soc Mag Reson Med. vol. 11; 2004. p. 310.

Edelman R, Leloudas N, Pang J, Bailes J, Merrell R, Koktzoglou I. Twofold improved tumor-to-brain contrast using a novel T1 relaxation-enhanced steady-state (T1RESS) MRI technique. Sci Adv 2020;6(44).

Edelman. ""Push-Button" Non-Contrast MR Angiography using Balanced T1 Relaxation-Enhanced Steady-State (bT1RESS)" Mar. 2021; Web [online]. [retrieved Jul. 22, 2024]. Retrieved from the Internet: <URL: https://www.ncbi.nlm.nih.gov/pmc/articles/PMC7718305/ > Entire Document.

International Search Report and Written Opinion under date of mailing of Aug. 21, 2024, in connection with PCT/US2024/027965, 8 pgs.

* cited by examiner

SELECT TIME INTERVAL FOR CONTRAST-MODIFYING (CM) RF PULSES ⟶ 202

DETERMINE FLIP ANGLE FOR CM RF PULSES BASED ON MINIMUM ERNST ANGLE FOR SET OF ONE OR MORE BACKGROUND TISSUES TO BE SUPPRESSED ⟶ 204

ACQUIRE MR DATA USING STEADY-STATE PULSE SEQUENCE INCLUDING CM RF PULSES ⟶ 206

GENERATE IMAGE USING MR DATA ⟶ 208

DISPLAY IMAGE ⟶ 210

SYSTEM AND METHOD FOR T$_1$ RELAXATION ENHANCED STEADY-STATE MRI

CROSS-REFERENCE TO RELATED APPLICATIONS

This application is a continuation-in-part of U.S. patent application Ser. No. 17/911,809, filed on Sep. 15, 2022, entitled "System and Method for T1 Relaxation Enhanced Steady-State MRI," which is a 371 application of PCT/US2021/021895 filed on Mar. 11, 2021, which claims priority to U.S. Ser. No. 62/991,181 filed Mar. 18, 2020, and entitled "System and Method for T1 Relaxation Enhanced Steady-State MRI," each of which are incorporated by reference herein in their entirety for all purposes."

BACKGROUND

The present disclosure relates to magnetic resonance imaging (MRI) and systems, more particularly, the present disclosure relates to systems and methods for magnetic resonance imaging (MRI).

When a substance such as human tissue is subjected to a uniform magnetic field (polarizing field B$_0$), the individual magnetic moments of the nuclei in the tissue attempt to align with this polarizing field, but precess about it in random order at their characteristic Larmor frequency. If the substance, or tissue, is subjected to a magnetic field (excitation field B$_1$) that is in the x-y plane and that is near the Larmor frequency, the net aligned moment, M$_z$, may be rotated, or "tipped", into the x-y plane to produce a net transverse magnetic moment M$_{xy}$. A signal is emitted by the excited nuclei or "spins", after the excitation signal B$_1$ is terminated, and this signal may be received and processed to form an image.

When utilizing these "MR" signals to produce images, magnetic field gradients (G$_x$, G$_y$, and G$_z$) are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

Magnetic resonance angiography (MRA) uses the magnetic resonance phenomenon to produce images of the human vasculature. To enhance the diagnostic capability of MRA, a contrast agent such as gadolinium can be injected into the patient prior to the MRA scan. The goal of this contrast enhanced (CE) MRA method is to acquire the central k-space views at the moment the bolus of contrast agent is flowing through the vasculature of interest in order to benefit from improved contrast. That is, collection of the central lines of k-space during peak arterial enhancement, therefore, is key to the success of a CE-MRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins.

Recently, a rare and serious pathology involving fibrosis of skin, joints, eyes, and internal organs referred to as nephrogenic systemic fibrosis ("NSF") has been correlated to the administration of gadolinium-based contrast agents to patients undergoing contrast-enhanced MRA studies. The link between gadolinium-based contrast agents and NSF is described, for example, by P. Marckmann, et al., in "Nephrogenic Systemic Fibrosis: Suspected Causative Role of Gadodiamide Used for Contrast-Enhanced Magnetic Resonance Imaging," J. Am. Soc. Nephrol, 2006; 17 (9):2359-2362. As a result of the increased incidence of NSF, methods for MRA that do not rely on the administration of a contrast agent to the patient have become an important field of research. However, current methods for non-contrast angiography are limited in their utility.

Steady-state gradient-echo acquisition techniques such as balanced steady-state free precession (bSSFP) are widely used in MRI because they provide a highly efficient acquisition with excellent signal-to-noise ratio. Steady-state MRI techniques permit the use of very short repetition times (TR), which makes them extremely efficient. Tissue contrast in steady-state acquisitions is dependent on the ratio T$_2$/T$_1$ of the tissue relaxation times. Certain tissues, specifically fluid, blood and fat, typically appear bright in the steady-state images. The bSSFP pulse sequence is commonly used in cardiovascular imaging and may be used to produce high signal from flowing blood, as well as from fluid-containing structures and fat. It is routinely used for cine and delayed enhanced imaging of the heart, for electrocardiogram (ECG)-gated NCMRA (non-contrast MR angiography) techniques such as quiescent interval slice-selective (QISS) and flow sensitive dephasing, as well as for niche applications such as constructive interference steady-state (CISS) for imaging of the inner ear structure. Balanced steady-state free precession techniques also have the property of being intrinsically compensated with respect to flow-induced phase shifts, so that flowing blood appears bright. Consequently, these techniques are routinely used to image the flow of blood in the heart (e.g., "cineangiography") and are used as the readout for non-contrast MR angiography techniques such as quiescent interval slice-selective MRA.

In order to maximize the conspicuity of flowing blood using steady-state sequences, it is necessary to suppress the signal intensity of other tissues, especially fat and fluid. Fat can be suppressed using chemical shift selective radiofrequency (RF) pulses or by periodically interrupting the echo train using pulses sequences such as fast interrupted steady-state (FISS).

Other examples of variations of the bSSFP pulse sequences in which the echo train is intermittently paused and restarted to improve fat suppression are described in Scheffler K, Heid O, Hennig J. Magnetization preparation during the steady state: fat saturated 3D TrueFISP. Magn Reson Med 2001; 45(6):1075-1080 and Derbyshire J A, Herzka D A, McVeigh ER. S5FP: spectrally selective suppression with steady state free precession. Magn Reson Med 2005; 54(4):918-928; U.S. Pat. No. 7,253,620, Aug. 7, 2007. However, suppression of signal from fluid is problematic. One can suppress fluid signal using a fluid attenuation inversion recovery (FLAIR) technique, but this requires the use of a very long inversion time (e.g., >2 see) that greatly reduces scan efficiency and prolongs scan time. Fluid signal may also be attenuated using a diffusion weighted preparation module, but this greatly increases the motion sensitivity of the pulse sequence and suppresses intravascular signal. It would therefore be desirable to provide a method for MRA that provides modified tissue contrast and fluid signal suppression and that can be used for contrast-enhanced and non-contrast angiography.

Although the tissue $T_1$ relaxation time of an enhancing tissue is reduced by the administration of contrast agent, so is the tissue $T_2$ relaxation time with the result that the ratio $T_2/T_1$, which determines tissue signal with steady-state MRI, is unchanged. In order to obtain $T_1$ weighting for imaging tissue enhancement following the administration of an extracellular paramagnetic contrast agent, bSSFP traditionally incorporates a preparatory 90° saturation recovery (e.g., for first-pass contrast-enhanced perfusion imaging) or 180° inversion recovery (IR) RF pulse (e.g., for imaging of delayed myocardial enhancement). These preparatory RF pulses are followed by a waiting period of at least a few hundred milliseconds prior to data collection. The use of a large flip angle preparatory RF pulse has the drawback of reducing the SNR and causing flow saturation artifacts with NCMRA. Moreover, the lengthy waiting period greatly diminishes scan efficiency compared with an unmodified bSSFP sequence. Consequently, steady-state pulse sequences are not typically useful for contrast-enhanced MRA, where a short scan time is needed in order to image the passage of contrast agent through the blood vessels of interest. As a result, contrast-enhanced MRI is almost always performed using fast low angle shot (FLASH) pulse sequences, even though the SNR is much lower than with a steady-state pulse sequence.

Contrast-enhanced MRI scans are typically acquired using a short repetition time $T_1$-weighted spoiled gradient-echo acquisition that applies a low flip angle excitation, where the low flip angle excitation only yields a fraction of the signal-to-noise ratio that could be obtained using a short repetition steady-state acquisition with a larger flip angle excitation. It would therefore also be desirable to provide a method for contrast-enhanced steady-state MRI where additional $T_1$ weighting is introduced without substantially reducing scan efficiency.

SUMMARY

In accordance with an embodiment, a method for equilibrium phase contrast-enhanced magnetic resonance (MR) angiography using an extracellular MR contrast agent administered to a subject includes performing, using a magnetic resonance imaging (MRI) system, a balanced $T_1$ relaxation enhanced steady-state pulse sequence to acquire MR data from a region of interest of the subject during an equilibrium phase of contrast enhancement after a first pass of the extracellular contrast agent through the region of interest. The balanced $T_1$ relaxation enhanced steady-state pulse sequence includes a $T_1$-weighted magnetization preparation comprising at least one contrast modifying (CM) radio frequency (RF) pulse, and a single-shot balanced steady-state free precession (bSSFP) readout applied after $T_1$-weighted magnetization preparation, the bSSFP readout comprising a plurality of excitation RF pulses and configured to acquire the MR data including a center of k-space in a plurality of echoes corresponding to the plurality of excitation RF pulses. The balanced $T_1$ relaxation enhanced steady-state pulse sequence further includes a time interval between the $T_1$-weighted magnetization preparation and the acquisition of the center of k-space, wherein the time interval is determined based on a $T_1$ relaxation time of a contrast-enhanced blood pool and a flip angle of the at least one CM RF pulse and the time interval is configured to maximize a contrast between the contrast enhanced blood pool and at least one other tissue in the region of interest. The method further includes generating an angiographic image of the region of interest of the subject based on the acquired MR data, wherein blood vessels in the region of interest appear brighter than background tissues.

In accordance with another embodiment, a magnetic resonance imaging (MRI) system includes a magnet system configured to generate a polarizing magnetic field about at least a portion of a subject, a plurality of gradient coils configured to apply at least one gradient field to the polarizing magnetic field, a radio frequency (RF) system configured to apply an excitation field to the subject and to receive MR data from the subject and a computer system. The computer system is programmed to direct the plurality of magnetic gradient coils and the RF system to perform a balanced $T_1$ relaxation enhanced steady-state pulse sequence to acquire MR data from a region of interest of the subject during an equilibrium phase of contrast enhancement after a first pass of the extracellular contrast agent through the region of interest. The balanced $T_1$ relaxation enhanced steady-state pulse sequence includes a $T_1$-weighted magnetization preparation comprising at least one contrast modifying (CM) radio frequency (RF) pulse, and a single-shot balanced steady-state free precession (bSSFP) readout applied after the $T_1$-weighted magnetization preparation, the bSSFP readout comprising a plurality of excitation RF pulses and configured to acquire the MR data including a center of k-space in a plurality of echoes corresponding to the plurality of excitation RF pulses. The $T_1$ relaxation enhanced steady-state pulse sequence includes a time interval between the $T_1$-weighted magnetization preparation and the acquisition of the center of k-space, wherein the time interval is determined based on a $T_1$ relaxation time of a contrast-enhanced blood pool and a flip angle of the at least one CM RF pulse, and the time interval is configured to maximize a contrast between the contrast enhanced blood pool and at least one other tissue in the region of interest. The computer system is further programmed to generate an angiographic image of the region of interest of the subject based on the acquired MR data, wherein blood vessels in the region of interest appear brighter than background tissues.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
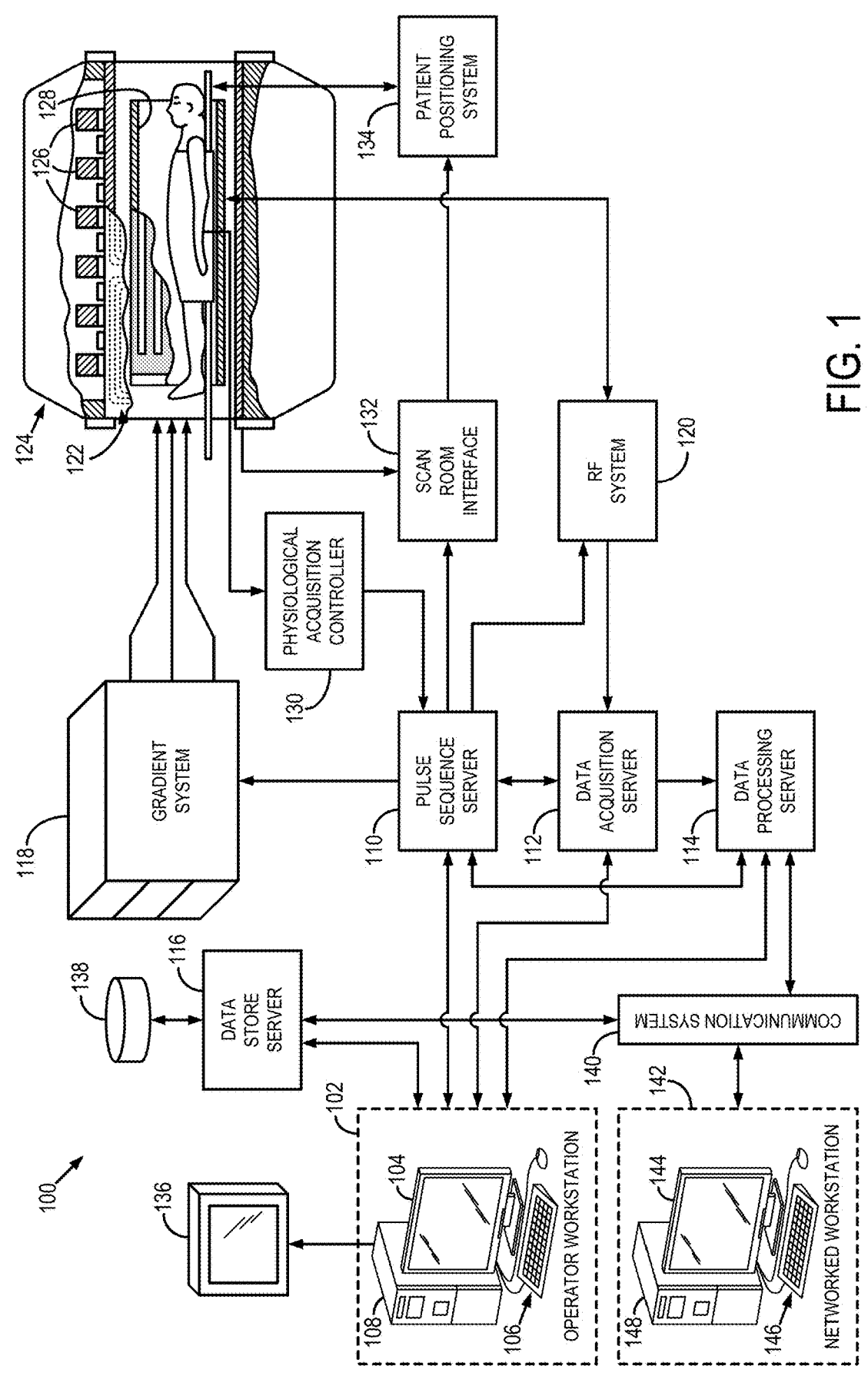
FIG. 1 is a block diagram of an example magnetic resonance imaging (MRI) system in accordance with an embodiment.

Referring now to FIG. 1, the disclosed systems and methods may be implemented using or designed to accompany a magnetic resonance imaging ("MRI") system 100, such as is illustrated in FIG. 1. The MRI system 100 includes an operator workstation 102, which will typically include a display 104, one or more input devices 106 (such as a keyboard and mouse or the like), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers, including a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms to perform the prescribed scan are produced and applied to the gradient system 118, which excites gradient coils in an assembly 122 to produce the magnetic field gradients $G_x$, $G_y$, $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2};$$

<div align="right">Eqn. 1</div> and the phase of the received magnetic resonance signal may also be determined according to the following relationship:

$$\varphi = \tan^{-1}\left(\frac{Q}{I}\right).$$

<div align="right">Eqn. 2</div>

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heartbeat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data;

performing other image reconstruction techniques, such as iterative or backprojection reconstruction techniques; applying filters to raw k-space data or to reconstructed images; generating functional magnetic resonance images; calculating motion or flow images; and so on.

Images reconstructed by the data processing server 114 are conveyed back to the operator workstation 102. Images may be output to operator display 112 or a display 136 that is located near the magnet assembly 124 for use by attending clinician. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse or the like), and a processor 148. The networked workstation 142 may be located within the same facility as the operator workstation 102, or in a different facility, such as a different healthcare institution or clinic. The networked workstation 142 may include a mobile device, including phones or tablets.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchange between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

The present disclosure describes a system and method for $T_1$ relaxation enhanced steady state ($T_1$RESS) MR imaging that suppresses fluid signal and modifies tissue contrast. In particular, tissue contrast in a steady-state acquisition is altered by periodically applying a contrast-modifying (CM) low flip angle RF pulse during the steady-state acquisition. The $T_1$RESS technique enables the efficient acquisition of steady-state MRI with a flexible degree of $T_1$ weighting. In an embodiment, the disclosed system and method may be used to enable high-quality non-contrast ungated MR angiography by suppressing fluid signal that might otherwise obscure the signal from arterial blood. In another embodiment, the system and method may also be used to suppress fluid signal on cine images of the heart, which might otherwise mimic the appearance of flowing blood. In yet another embodiment, the system and method may be used for contrast-enhanced MRI. The repeated application of a CM RF pulse introduces additional $T_1$ weighting and, therefore, makes the steady-state sequence sensitive to the effects of a paramagnetic contrast agent. For contrast-enhanced MRI, the $T_1$RESS technique provides marked improvement in image quality, contrast-to-noise ratio, and vascular conspicuity compared with conventional imaging techniques. For non-contrast magnetic resonance angiography (NCMRA), the $T_1$RESS technique depicts vascular anatomy and pathology with excellent image quality and spatial resolution comparable to CT angiography, using a workflow that obviates the need for scout imaging, contrast agents, breath-holding, or cardiac synchronization.

Figure 2:
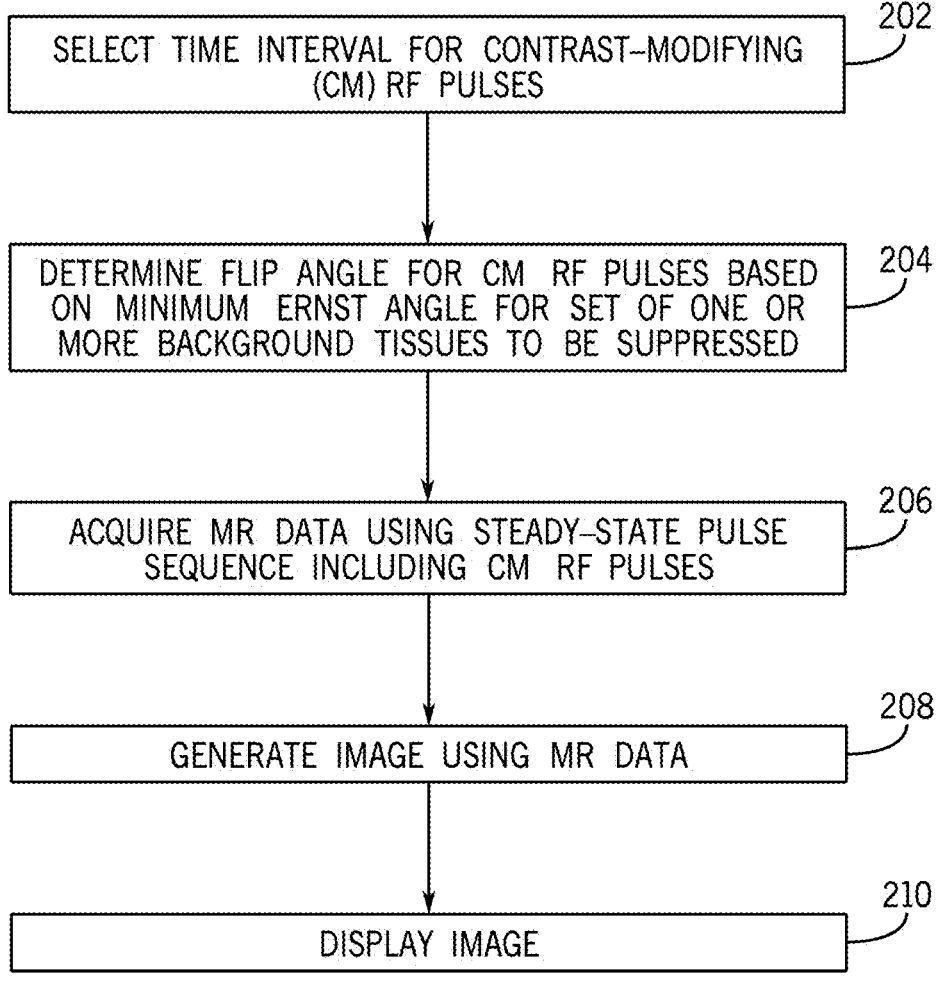
FIG. 2 illustrates a method for creating a magnetic resonance (MR) image of a subject in accordance with an embodiment.

FIG. 2 illustrates a method for creating a magnetic resonance (MR) image of a subject in accordance with an embodiment. As mentioned above, the system and method described herein for $T_1$ relaxation enhanced steady-state imaging combines a steady-state pulse sequence with periodically applied contrast-modifying (CM) partial saturation RF pulses to modify tissue contrast and suppress fluid signal. At block 202, a time interval, $\tau$, is selected for periodic application of a CM RF pulse during a steady-state acquisition. The time interval, $\tau$, is the time interval between application of successive CM RF pulses. The time interval, $\tau$, may be selected to provide an efficient imaging sequence and sufficient $T_1$ contrast. In an embodiment, the CM RF pulses are applied infrequently, for example, at intervals greater than 50 ms (i.e., $\tau > 50$ ms), so that scan efficiency is maintained, and scan time is only marginally increased. In another embodiment, the CM RF pulses may be applied at regular intervals on the order of 100 to 400 ms throughout the duration of the steady-state acquisition.

At block 204, the flip angle ($\alpha_{CM}$) for the CM RF pulses that are applied at the periodic intervals, $\tau$, is determined based on a minimum Ernst angle for a set of one or more background tissues in the region of interest that the CM RF pulse is used to suppress with respect to a tissue of interest. In one embodiment, the CM RF pulses have a flip angle, $\alpha_{CM}$, that is greater than half the minimum Ernst angle of the set of one or more background tissues as given by:

$$\alpha_{CM} > 0.5 \times \cos^{-1}\left(e^{-\tau/T_{1min}}\right) \qquad \text{Eqn. 3}$$

where $\alpha_{CM}$ is the flip angle in degrees of the CM RF pulse, $\cos^{-1}$ is the inverse cosine function yielding degrees (not radians), e is the mathematical constant approximately equal to 2.71828, T is the time interval between application of successive CM RF pulses, and $T_{1min}$ is the shortest longitudinal relaxation time in the set of one or more background tissues the CM RF pulse should suppress. In this embodiment, the factor, 0.5, was chosen to be low for additional suppression by the imaging readout, and to account for other factors such as, for example, inflow which may artificially enhance the appearance of inflowing blood, while still providing adequate blood-to-background contrast. The same flip angle may be used for each CM RF pulse throughout the steady-state acquisition or one or more CM RF pulses applied during an acquisition may have a different flip angle. In one embodiment, the background tissue to be suppressed is fluid and the tissue of interest is blood. In another embodiment, the background tissue to be suppressed is unenhanced myocardium and the tissue of interest is enhanced myocardium. In yet another embodiment, the background tissue to be suppressed is normal tissue and the tissue of interest is abnormally enhancing tissue such as a tumor or inflammation.

At block 206, MR data is acquired by performing a steady-state pulse sequence including periodically applied CM RF pulses (a $T_1$ relaxation enhanced steady-state sequence) using, for example, an MRI system (e.g., MRI system 100 shown in FIG. 1). As described above, CM RF pulses are applied at the selected time interval, $\tau$, with the selected flip angle, $\alpha_{CM}$. In an embodiment, the CM RF pulses may be slice selective. The steady-state pulse sequence may be, for example, an un-balanced steady-state free precession (SSFP) pulse sequence, a balanced steady-state free precession (bSSFP) sequence, a fast interrupted steady-state (FISS) sequence, or other steady-state pulse sequence type such as a fast imaging with steady-state precession (FISP) sequence, a spoiled gradient echo sequence or a fast low angle shot (FLASH) sequence. The steady-state pulse sequence may be configured for a two-dimensional (2D) or three-dimensional (3D) acquisition. In order to avoid disruption of the steady-state magnetization when each CM RF pulse is applied during the steady-state acquisition, in an embodiment the CM RF pulse may be preceded by an $\alpha/2$ store RF pulse (where a is the imaging flip angle) to flip the magnetization along the longitudinal axis, followed by another $\alpha/2$ restore RF pulse of opposite polarity to flip the magnetization back into the transverse plane.

At block 208, an image (e.g., an angiogram) may be generated using the acquired MR data from block 206. As mentioned above, the generated image will have fluid signal suppression and $T_1$ contrast. The image may be generated using known reconstruction methods. At block 210, the image may be displayed to a user on a display (e.g., display 104, 136 or 144 shown in FIG. 1). The image may also be stored in in memory or data storage of, for example, an MRI system (e.g., the MRI system 100 of FIG. 1) or other computer system.

Figure 3:
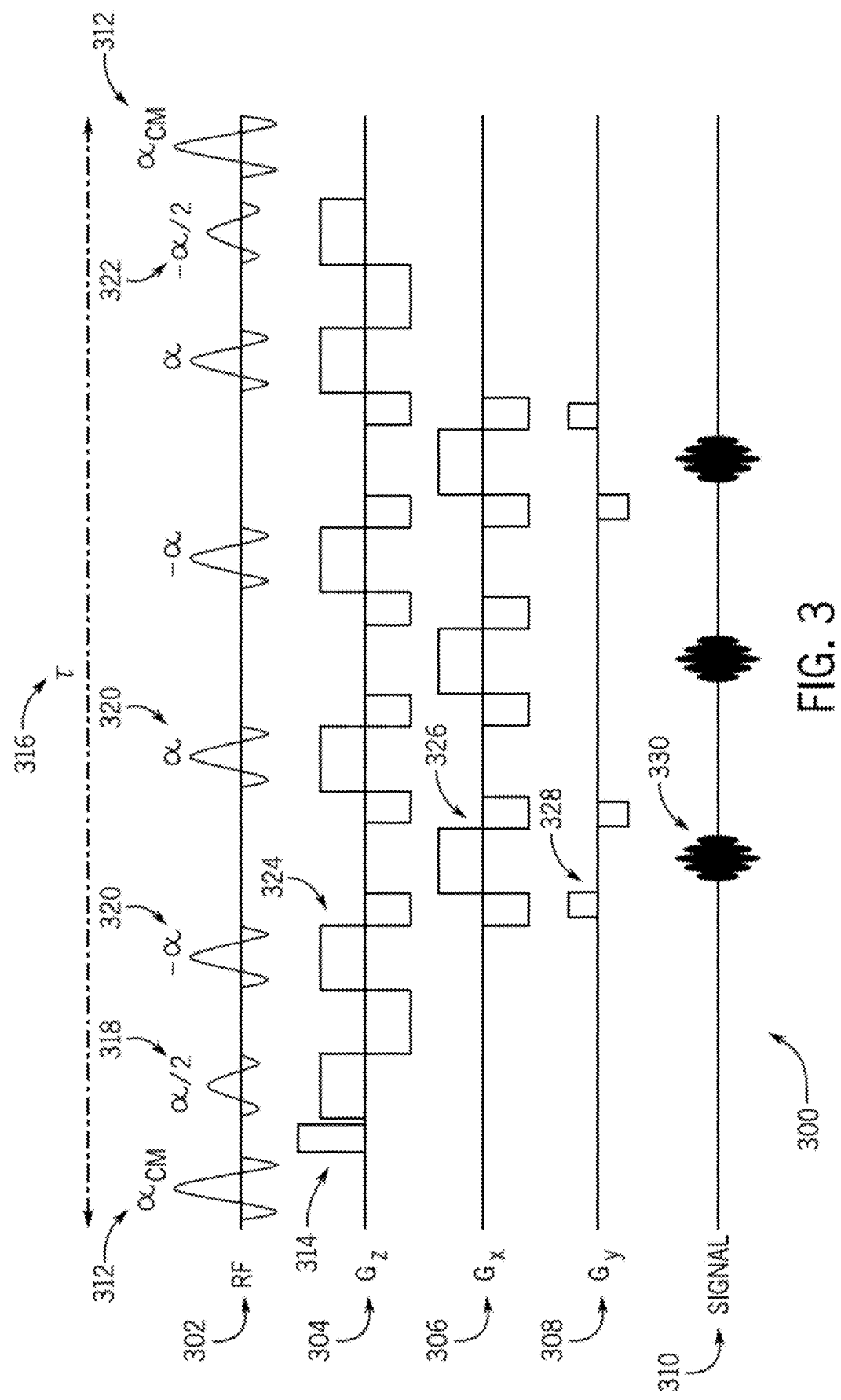
FIG. 3 is a pictorial representation of a $T_1$ relaxation enhanced steady-state ($T_1$RESS) pulse sequence in accordance with an embodiment.

As mentioned, various steady-state pulse sequences may be combined with the periodically applied CM RF pulses to provide a $T_1$ relaxation enhanced steady-state technique. FIG. 3 is a pictorial representation of a $T_1$ relaxation enhanced steady-state ($T_1$RESS) pulse sequence in accordance with an embodiment. In FIG. 3, the steady-state pulse sequence is a balanced steady-state free precession (bSSFP) sequence. The $T_1$ relaxation enhanced steady-state sequence 300 provides the capability to flexibly modulate the amount of $T_1$ weighting in an MR image while maintaining high scan efficiency. In FIG. 3, axis 302 is the axis for radio frequency (RF) pulses, axis 304 is the slice-selection direction, axis 306 is the frequency encoding direction, axis 308 is the phase encoding direction, and axis 310 is the generated signal. The sequence 300 uses an interrupted balanced steady-state free precession readout. In accordance with an embodiment, to suppress signal from one or more background tissues in a region of interest, for example, fluid, and to modify tissue contrast, a CM RF pulse 312 with a flip angle $\alpha_{CM}$ is applied followed by gradient spoiling using a gradient 314 in the slice-selection direction 304. As discussed above, the time interval, T 316 (the time interval between application of successive CM RF pulses 312), is selected for periodic application of a CM RF pulse 312 during a steady-state acquisition and the flip angle $\alpha_{CM}$ for the CM RF pulse 312 is selected according to $\alpha_{CM} > 0.5 \times \cos^{-1}(e^{-\tau/T_{1min}})$, where $\cos^{-1}$ is the inverse cosine function yielding degrees (not radians) and $T_{1min}$ is the shortest longitudinal relaxation time in the set of one or more background tissues the CM RF pulse is used to suppress. Accordingly, the flip angle $\alpha_{CM}$ for each CM RF pulse is determined based on a minimum Ernst angle for the set of one or more background tissues in the region of interest that the CM RF pulse 312 is used to suppress with respect to a tissue of interest.

In an embodiment, an $\alpha/2$ RF pulse 318 (where $\alpha$ is the imaging flip angle) is applied after the CM RF pulse 312 and gradient spoiler 314 to restore the magnetization in the longitudinal axis to the transverse plane prior to application of the $\pm\alpha$ imaging RF pulses 320. An $-\alpha/2$ pulse 322 is applied immediately prior to each application of the CM RF pulse 312 to store the magnetization in the transverse plane to the longitudinal axis. While the magnetization is stored along the longitudinal axis, the CM RF pulse 312 may be applied without disrupting the steady-state magnetization.

In FIG. 3, slice-selection gradients 324 are also applied in the slice direction 304 to excite a slice in the subject, frequency-encoding gradient 326 are applied in the frequency-encoding direction 306 and phase-encoding gradients 328 are applied on the phase-encoding direction 308. While one $\tau$ for the sequence 300 is shown, it should be understood that the sequence would repeat until all k-space data are sampled, with CM RF pulses 312 applied at the time interval, $\tau$, throughout the steady-state acquisition. While three imaging echo signals 330 following the $\pm\alpha$ imaging RF pulses 320 (i.e., n=3) are shown for the sequence 300 between the CM RF pulses, it should be understood that the number of $\pm\alpha$ pulses followed by echo signals may range from 1 to several hundred.

In some aspects, using a radial k-space trajectory offers improvements over a Cartesian k-space trajectory. For example, the need for a waiting period may be obviated by use of a radial k-space trajectory and optimized azimuthal view angles that suppress image artifacts. In some aspects, when multiple bSSFP readouts are collected (i.e., n>1), radial sampling is less sensitive than Cartesian sampling to artifacts caused by mild signal fluctuations arising from the interrupted nature of the contrast-modified pulse sequence, for example, the sequence in FIG. 3. With Cartesian k-space sampling, these signal fluctuations produce ghost artifacts in the phase-encoding direction. Conversely, these small signal variations produce minimal to no apparent artifacts with radial sampling. By distributing the signal fluctuations over a large (>540 degrees) azimuthal range of radial views, radial sampling is highly effective at minimizing image artifacts due to the signal fluctuations. In other aspects, due to oversampling of central k-space, radial sampling is less sensitive than Cartesian sampling to motion and arterial pulsation artifacts.

The pulse sequence described with respect to FIG. 3 can also be combined with other imaging techniques. In one non-limiting example, the described technique can be combined with cine imaging which may be used to portray multiple phases of the cardiac cycle. In another example, data acquisition performed using the described technique may be accelerated using accelerated imaging techniques, such as radial under sampling, compressed sensing, or simultaneous multi-slice acquisitions. In another example, the described technique may be combined with motion reduction techniques such as navigator gating or motion correction. In another example, two or more echoes may be acquired to permit the use of a Dixon reconstruction technique to create water-only and fat-only images.

In an embodiment, magnetic resonance (MR) images of a subject may be generated by performing a steady-state pulse sequence to acquire MR data from a region of interest in the subject. The steady-state pulse sequence may be performed using an MRI system. The steady-state pulse sequence includes a contrast-modifying (CM) radio frequency (RF) pulse applied periodically at a predetermined time interval followed by a gradient spoiler pulse. In an embodiment, the predetermined time interval may be greater than 50 ms. The CM RF pulse has a flip angle with a value determined based on a minimum Ernst angle for a set of one or more background tissues in the region of interest that the CM RF pulse is configured to suppress with respect to a tissue of interest. An image with $T_1$ contrast may be generated based on the acquired MR data. In an embodiment, the generated image may be displayed on a display. The set of one or more background tissues may include, for example, a fluid, an unenhanced myocardium, or a normal tissue and the tissue of interest may include, for example, blood, enhanced myocardium, or an abnormally enhancing tissue, respectfully. The abnormally enhancing tissue may be, for example, a tumor or inflammation.

In one embodiment, the flip angle of the CM RF pulse has a value greater than half the minimum Ernst angle for the set of one or more background tissues in the region of interest that the CM RF pulse is configured to suppress with respect to the tissue of interest and is determined using Eqn. 3 above, namely, $\alpha_{CM} > 0.5 \times \cos^{-1}(e^{-\tau/T_{1min}})$, where $\alpha_{CM}$ is the flip angle in degrees of the CM RF pulse, $\cos^1$ is the inverse cosine function yielding degrees (not radians), e is the mathematical constant approximately equal to 2.71828, $\tau$ is the predetermined time interval, and $T_{1min}$ is the shortest longitudinal relaxation time in the set of one or more background tissues the CM RF pulse is configured to suppress. In an embodiment, the steady-state pulse sequence also includes a $\alpha/2$ store RF pulse applied prior to the CM RF pulse and an $\alpha/2$ restore RF pulse applied following to the CM RF pulse. The CM RF pulse may be slice selective. In various embodiments, the steady-state pulse sequence may be, for example, a steady-state free precession (SSFP) pulse sequence, a balanced steady-state free precession (bSSFP) pulse sequence, a fast interrupted steady-state (FISS) pulse sequence, a gradient echo based pulse sequence, or a fast imaging with steady-state precession (FISP) pulse sequence. The balanced steady-state free precession pulse sequence may be used, for example, for a cine acquisition or an MR angiography acquisition. In another embodiment, the steady-state pulse sequence may be accelerated using radial undersampling, compressed sensing, or simultaneous multi-slice. In yet another embodiment, performing the steady-state pulse sequence may include performing a motion reduction technique. In various other embodiments, the steady-state pulse sequence may be performed before, during, or after the administration (e.g., injection) of a contrast agent (e.g., a paramagnetic contrast agent such as gadolinium).

As mentioned, the $T_1$RESS method described above with respect to FIGS. 2 and 3 can be used for performing contrast-enhanced MRI such as, for example, CEMRA. However, typically, the central k-space views (or central lines of k-space) are acquired during the first pass of a paramagnetic extracellular gadolinium based contrast agent (GBCA) during peak intravascular signal enhancement. This is because the angiographic image quality can be substantially degraded (i.e., non-diagnostic) when data acquisition is delayed until the equilibrium phase of contrast enhancement (i.e., after the first pass of the GBCA). The degraded image quality is because the $T_1$ relaxation time of the blood pool is several-fold longer during the equilibrium phase which has a reduced concentration of contrast agent in the blood pool than during the first pass of the GBCA, when the contrast agent is far more concentrated in the blood pool. In some embodiments, a $T_1$RESS-based technique can be provided that can advantageously enable equilibrium phase contrast-enhanced MRA as described below with respect to FIGS. 4-6.

In some embodiments, a balanced $T_1$RESS (bT$_1$RESS) pulse sequence for equilibrium phase contrast-enhanced MRA can be provided that combines 1) a $T_1$-weighted magnetization preparation having at least one CM RF pulse and that is configured to impart $T_1$ weighting and suppress background tissues, and 2) a bSSFP readout (or data acquisition module) applied after the $T_1$-weighted magnetization preparation. Advantageously, the equilibrium phase bT$_1$RESS pulse sequence can be configured to acquire the center of k-space (or central view of lines of k-space) during the equilibrium phase of contrast enhancement for a paramagnetic extracellular contrast agent, for example, a gadolinium-based contrast agent. Accordingly, the bSSFP readout can be applied after the first pass of the extracellular contrast agent through the region of interest of the subject and therefore, does not require matching the sequence timing to the first pass of the extracellular contrast agent through the region of interest. The equilibrium phase bT$_1$RESS pulse sequence can include a time interval, t, applied between the $T_1$-weighted magnetization preparation and the acquisition of the center of k-space that can be configured to maximize contrast between the contrast-enhanced blood pool and one or more background tissue(s). In some embodiments, the time interval, t, may be predetermined and may be based on an expected $T_1$ relaxation time of the blood pool (e.g., either estimated or measured) during the equilibrium phase (i.e., after the first pass of the extracellular contrast agent) and a flip angle of the at least one CM RF pulse of the $T_1$-weighted magnetization preparation. The equilibrium phase bT$_1$RESS pulse sequence can also include a waiting period applied between the $T_1$-weighted magnetization preparation and the bSSFP readout. The bSSFP readout can include a single-shot echo train. In some embodiments, the equilibrium phase bT$_1$RESS pulse sequence can be synchronized to the cardiac cycle. In some embodiments, the single shot echo train of the bSSFP readout can be synchronized to the quiescent phase of the cardiac cycle. The MR data acquired with the equilibrium phase bT$_1$RESS pulse sequence may be used to generate an angiographic image of the region of interest of the subject.

Advantageously, the disclosed method for equilibrium phase contrast-enhanced MRA using a bT$_1$RESS pulse sequence can produce diagnostic quality angiographic images for an extended duration (e.g., up to 30 minutes) after the administration of the extracellular contrast agent. The disclosed equilibrium phase bT$_1$RESS technique can prolong the useful duration of blood pool enhancement from the extracellular contrast agent (e.g., a gadolinium based contrast agent). By enabling imaging during the equilibrium phase of contrast enhancement, there is no risk of obtaining a poor quality scan from missing the first pass of the extracellular contrast agent. The disclosed equilibrium phase bT$_1$RESS technique can also provide significantly better image quality than prior CEMRA techniques. In some embodiments, equilibrium phase CEMRA performed with the disclosed technique can be repeated as needed if the patient moves or fails to adequately breath-hold. The disclosed technique is highly efficient due to the use of a single-shot bSSFP readout, which permits the use of either breath-holding or free-breathing acquisitions. In some embodiments, the disclosed equilibrium phase bT$_1$RESS technique can be used perform equilibrium phase imaging of the entire heart within a breath-hold. In addition, the disclosed method for equilibrium phase contrast-enhanced MRA can be used to obtain an MR angiogram in clinical situations where the extracellular contrast agent was primarily given for a non-vascular indication. For example, the equilibrium phase bT$_1$RESS technique may be used to evaluate the extracranial carotid arteries following a contrast-enhanced brain MRI, or to evaluate the great vessels or pulmonary veins following a cardiac perfusion study. In some embodiments, for abdominal MRI, the equilibrium phase $bT_1RESS$ technique can be used to evaluate the patency of the portal or systemic veins, or to distinguish slow flow from thrombus. For non-cardiac applications, ECG gating is unnecessary. Therefore, the equilibrium phase $bT_1RESS$ shot repetition time can be substantially shortened and scan efficiency improved, allowing more slice coverage, shorter breath-hold-times, or improved spatial resolution.

The disclosed method for equilibrium phase contrast-enhanced MRA using a $bT_1RESS$ pulse sequence can also be arrhythmia-resistant. As mentioned, in some embodiments, the SSFP readout of the equilibrium phase $bT_1RESS$ sequence can be synchronized to the cardiac cycle (e.g., ECG-gated). In some embodiments, the $T_1$-weighted magnetization preparation of the equilibrium phase $bT_1RESS$ pulse sequence can be a saturation recovery magnetization preparation which can reset the longitudinal magnetization to zero at the start of each cardiac cycle. As a result, the MR signal remains constant from one cardiac cycle to the next, irrespective of variations in the RR interval. Consequently, unlike previously described techniques for ECG-gated CEMRA, the disclosed technique is highly resistant to ghost artifacts from arrhythmias. Moreover, as mentioned, the disclosed technique uses a single-shot readout which avoids the possibility of signal variations between shots and further reduces sensitivity to ghost artifacts.

Figure 4:
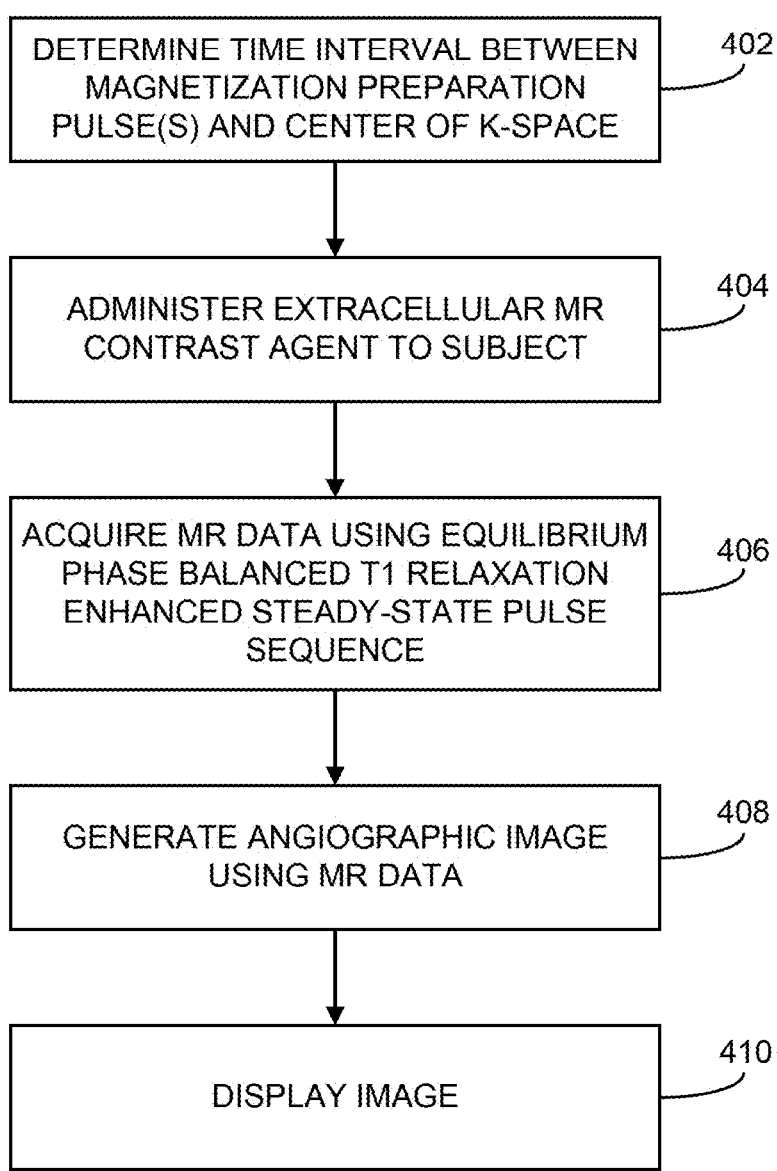
FIG. 4 illustrates a method for equilibrium phase contrast-enhanced MR angiography for a subject in accordance with an embodiment.

FIG. 4 illustrates a method for equilibrium phase contrast-enhanced MR angiography for a subject in accordance with an embodiment. At block 402, a time interval, t, between $T_1$-weighted magnetization preparation pulse(s) and acquisition of a center of k-space (or central view(s) of k-space) along the phase encoding direction for an equilibrium phase $bT_1RESS$ pulse sequence may be determined. In some embodiments, the minimum time interval ($t_{min}$) that will produce a diagnostic quality CEMRA during the equilibrium phase is a function of the expected $T_1$ relaxation time ($T1_{blood\ pool}$) of the blood pool during equilibrium phase, and the flip angle ($CM\alpha$) of the CM RF pulse(s) in the $T_1$ magnetization preparation of the equilibrium phase $bT_1RESS$ pulse sequence, and can be approximated as:

$$t_{min} \approx T1_{blood\ pool} \times (CM\alpha/90)^{1/3} \qquad \text{Eqn. 4}$$

where $CM\alpha$ is expressed in degrees, while $t_{min}$ and $T1_{blood\ pool}$ are expressed in milliseconds. In some embodiments, the minimum time interval $t_{min}$ may be selected as the value for the time interval, t. In some embodiments, a value for the time interval, t, may be selected that is longer than $t_{min}$, which can advantageously permit substantial recovery of the blood pool longitudinal magnetization so that the blood pool appears brighter than other tissues, which is a prerequisite for the creation of angiographic images. Accordingly, in some embodiments, the $T_1$ contrast between the bright enhancing blood pool and background tissues can be optimized by varying the t value based on the expected $T_1$ relaxation time of the contrast enhanced blood pool. In some embodiments, the expected $T_1$ relaxation time ($T1_{blood\ pool}$) of the blood pool during equilibrium phase can be estimated based on one or more factors including, for example, 1) contrast agent pharmacokinetic behavior, relaxation properties, or dose; 2) time delay after contrast agent infusion; 3) body-mass index; 4) cardiac function; 5) renal function; 6) empirical testing; or 7) published data. In some embodiments, the expected $T_1$ relaxation time ($T1_{blood\ pool}$) of the blood pool during equilibrium phase can be measured using quantitative mapping techniques such as, for example, MOLLI, shMOLLI, etc. For example, a separate scan may be performed shortly before a scan with the $bT_1RESS$ technique for equilibrium phase CEMRA is acquired in order to obtain a quantitative measurement of $T_1$ of the blood pool during the equilibrium phase. In some embodiments, the value of $t_{min}$ can be between 100 msec and 600 msec. In some embodiments, the time interval t, may be greater than the expected $T_1$ relaxation time of the contrast-enhanced blood pool.

At block 404, a paramagnetic extracellular contrast agent may be administered to the subject, for example, the extracellular contrast agent can be injected in the subject intravenously. In some embodiments, the extracellular contrast agent is a gadolinium based contrast agent (GBCA) such as, for example, gadobutrol. In some embodiments, the dose of the extracellular contrast agent can be selected to increase the $T_2/T_1$ ratio which can advantageously boost the blood pool signal. In some embodiments, the dose of extracellular contrast agent may be selected so as to at least double the $T_2/T_1$ ratio of the blood pool during the equilibrium phase of contrast enhancement.

At block 406, MR data can be acquired by performing the equilibrium phase $bT_1RESS$ pulse sequence with the selected time interval, t, between the $T_1$-weighted magnetization preparation and the acquisition of a center of k-space using, for example, an MRI system (e.g., MRI system 100 shown in FIG. 1). The equilibrium phase $bT_1RESS$ pulse sequence is applied after the first pass of the extracellular contrast agent. As mentioned, the equilibrium phase $bT_1RESS$ pulse sequence can include a $T_1$-weighted magnetization preparation and a single-shot bSSFP readout (or data acquisition module). The administration of a contrast agent shortens the $T_1$ relaxation time of the blood pool to a greater degree than it shortens the $T_2$ relaxation time of the blood pool. Since the signal intensity of a bSSFP pulse sequence depends primarily on the $T_2/T_1$ ratio, the administration of a contrast agent will substantially increase the signal intensity of the blood pool, which could be useful for MRA. However, background tissues that have both a long $T_1$ and a long $T_2$ relaxation time, including fluids and edema, will appear bright when imaged with a bSSFP pulse sequence and can look similar to enhancing blood vessels. The $T_1$-weighted magnetization preparation can be configured to impart $T_1$ weighting and to suppress signals from background tissues, for example, from tissues with long $T_2$. The $T_1$-weighted magnetization preparation can include one or more CM RF pulses. In some embodiments, as discussed further below with respect to FIG. 5, the magnetization preparation can include one CM RF pulse. In some embodiments, as discussed further below with respect to FIG. 6, the magnetization preparation can include three CM RF pulses. Each CM RF pulse in the $T_1$-weighted magnetization preparation has a flip angle ($CM\alpha$). In some embodiments, the value for $CM\alpha$ can be 90° which can provide a diagnostic level of blood pool signal over a wide range of time interval (t) values. In addition, for cardiac gated embodiments, when $CM\alpha$ is set to 90°, the longitudinal magnetization will be reset to zero at the start of each cardiac cycle. As a result, the MR signal remains constant from one cardiac cycle to the next, irrespective of variations in the RR interval. Consequently, as mentioned, the equilibrium phase $bT_1RESS$ technique can be made highly resistant to ghost artifacts from arrhythmias. In some embodiments, the value for $CM\alpha$ can be greater than 90°. In some embodiments, the $T_1$-weighted magnetization preparation is a saturation recovery magnetization preparation.

In some embodiments, the equilibrium phase $bT_1RESS$ pulse sequence can also include a waiting period between the $T_1$-weighted magnetization preparation and the single-shot bSSFP readout, and one or more other RF preparation pulses applied before the single-shot bSSFP readout. In some embodiments, the waiting period can be applied to fil in any dead time between the $T_1$-weighted magnetization preparation and the single-shot bSSFP readout in order to obtain the determined time interval, t. In some embodiments, other preparatory RF pulses may be applied before, the single-shot bSSFP readout. For example, one or more preparatory RF pulses can be applied before the bSSFP readout to drive the transverse magnetization towards the steady state. In some embodiments, a single $\alpha/2$ RF pulse or a series (or plurality) of constant-flip-angle dummy RF pulses (e.g., 32 dummy RF pulses) can be applied prior to the single-shot bSSFP readout to drive the transverse magnetization towards the steady-state. In some embodiments, a fat saturation RF pulse may be applied prior to the single-shot bSSFP readout. In some embodiments, fat suppression may be obtained by applying one or more chemical shift-selective RF pulses. In some embodiments, additional magnetization preparations may be applied such as, for example, a flow sensitive magnetization preparation, a $T_2$ preparation, a magnetization transfer preparation, or a $T1_{rho}$ preparation. As mentioned, a waiting period can be applied to fill in any dead time between the $T_1$-weighted magnetization preparation and the single-shot bSSFP readout in order to obtain the determined time interval, t. In an example, if the time interval, t, is 300 ms, and the time for a fat saturation and an $\alpha/2$ pulse is 20 ms, and the time from the first phase-encode to the central phase-encode is 100 ms, then a waiting period of 180 ms (300 ms-120 ms=180 ms) can be applied before the bSSFP readout.

The single-shot bSSFP readout can be a three dimensional bSSFP readout. The bSSFP readout can include a plurality of excitation (or imaging) RF pulses and can be used acquire MR data from the region of interest of the subject in an echo train comprising a plurality of echoes corresponding to the plurality of RF excitation pulses. In some embodiments, the plurality of excitation RF pulses can have a flip angle larger than 45°. The bSSFP readout is configured to collect (or acquire) MR data from the center of k-space (center k-space views) along a phase encoding direction during the equilibrium phase of contrast enhancement after completion of the first pass of the extracellular contrast agent through the region of interest. In other words, a first central phase encoding step can be acquired after the completion of the first pass of the extracellular contrast agent. In some embodiments, a Cartesian k-space trajectory may be used. In some embodiments, a non-Cartesian k-space trajectory may be used. In some embodiments, the MR data can be acquired in a single breath-hold. In some embodiments, the MR data can be acquired during free breathing. In some embodiments, the bSSFP readout can be accelerated using acceleration techniques including multi-dimensional acceleration techniques. For example, the bSSFP readout may be accelerated using Controller Aliasing in Parallel Imaging Results IN higher Acceleration (CAIPIRINHA), wave-CAIPIRINHA, 2D GRAPPA, or compressed sensing. In some embodiments, the bSSFP readout can be configured for a sampling bandwidth larger than 500 Hertz, an echo time (TE) less than 3 milliseconds, and a reconstruction voxel smaller than 30-mm³.

In some embodiments, the bSSFP readout can be cardiac gated (i.e., electrocardiographic (ECG)-gated), for example, using prospective gating. In some embodiments, the bSSFP readout can be synchronized to a diastolic phase of the cardiac cycle, for example, to the quiescent phase of the cardiac cycle. In some embodiments, the SSFP readout can be shorter in duration than the quiescent phase of the cardiac cycle. In some embodiments, a majority of the k-space views may be acquired during the quiescent phase of the cardiac cycle. Synchronizing the collection of MR data with the bSSFP readout to the quiescent phase of the cardiac cycle can freeze the effect of cardiac motion.

Advantageously, the single shot bSSFP readout of the disclosed equilibrium enhanced $bT_1RESS$ technique can be synchronized to the cardiac cycle irrespective of the length of the RR interval. In some embodiments, MR data can be acquired at both the end-systole and end-diastole to enable quantification of cardiac function.

At block 408, an angiographic image (e.g., an angiogram) may be generated using the acquired MR data from block 406. The angiographic image may be generated using known reconstruction methods. As mentioned, the blood pool is brighter than the background tissues (i.e., the blood pool is the brightest tissue) in the angiographic image generated using the MR data acquired using the equilibrium phase $bT_1RESS$ technique. In some embodiments, artificial intelligence may be used during reconstruction of the image to improve the signal-to-noise ratio, enhance image sharpness, or reduce image artifacts. At block 410, the generated angiographic image may be displayed to a user on a display (e.g., display 104, 136 or 144 shown in FIG. 1). The image may also be stored in a memory or data storage device of, for example, an MRI system (e.g., MRI system 100 shown in FIG. 1) or other computer systems.

Figure 5:
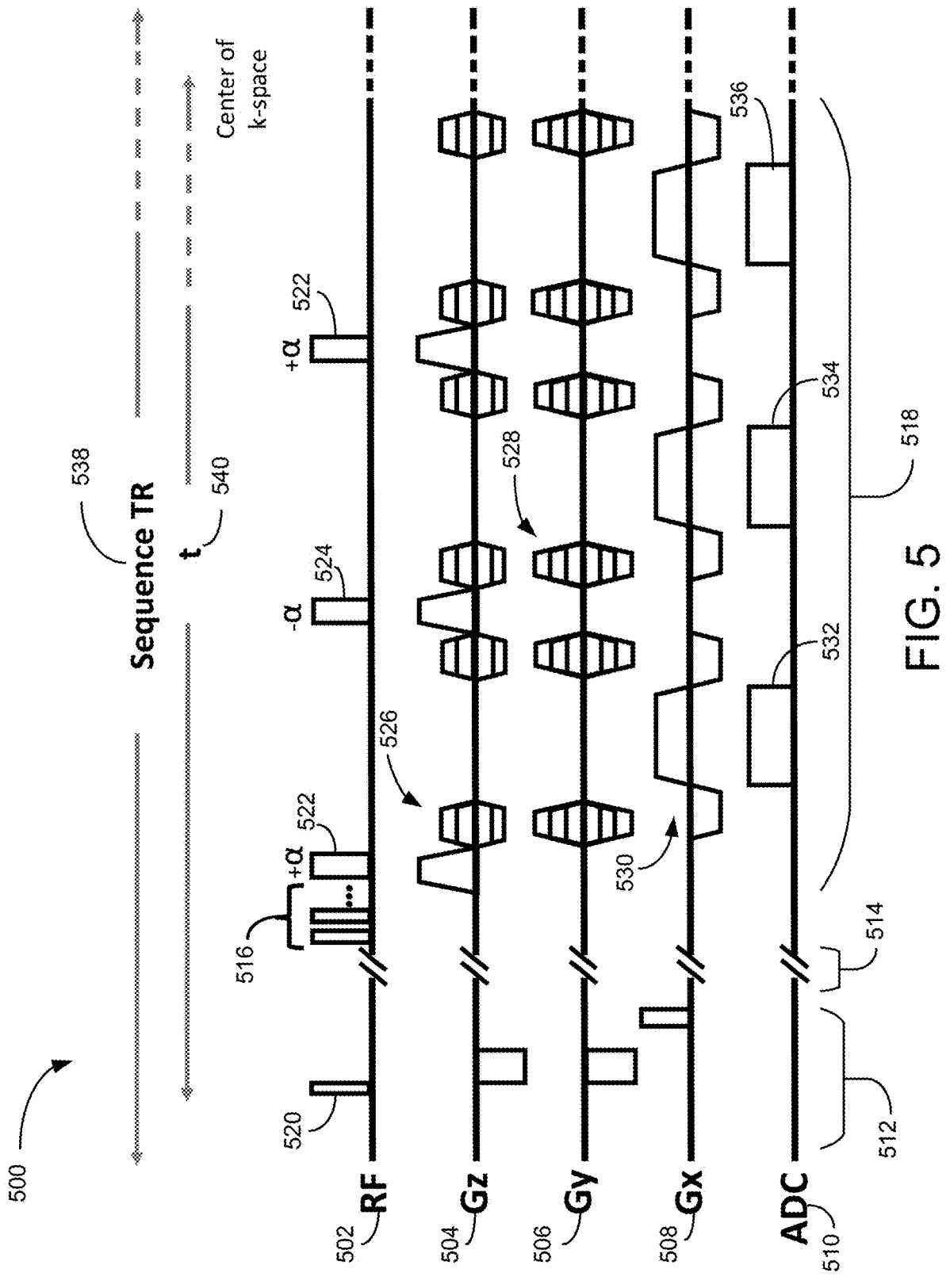
FIG. 5 is a pictorial representation of a balanced $T_1$ relaxation enhanced steady-state (bT$_1$RESS) pulse sequence for equilibrium phase contrast enhanced MR angiography in accordance with an embodiment.
Figure 6:
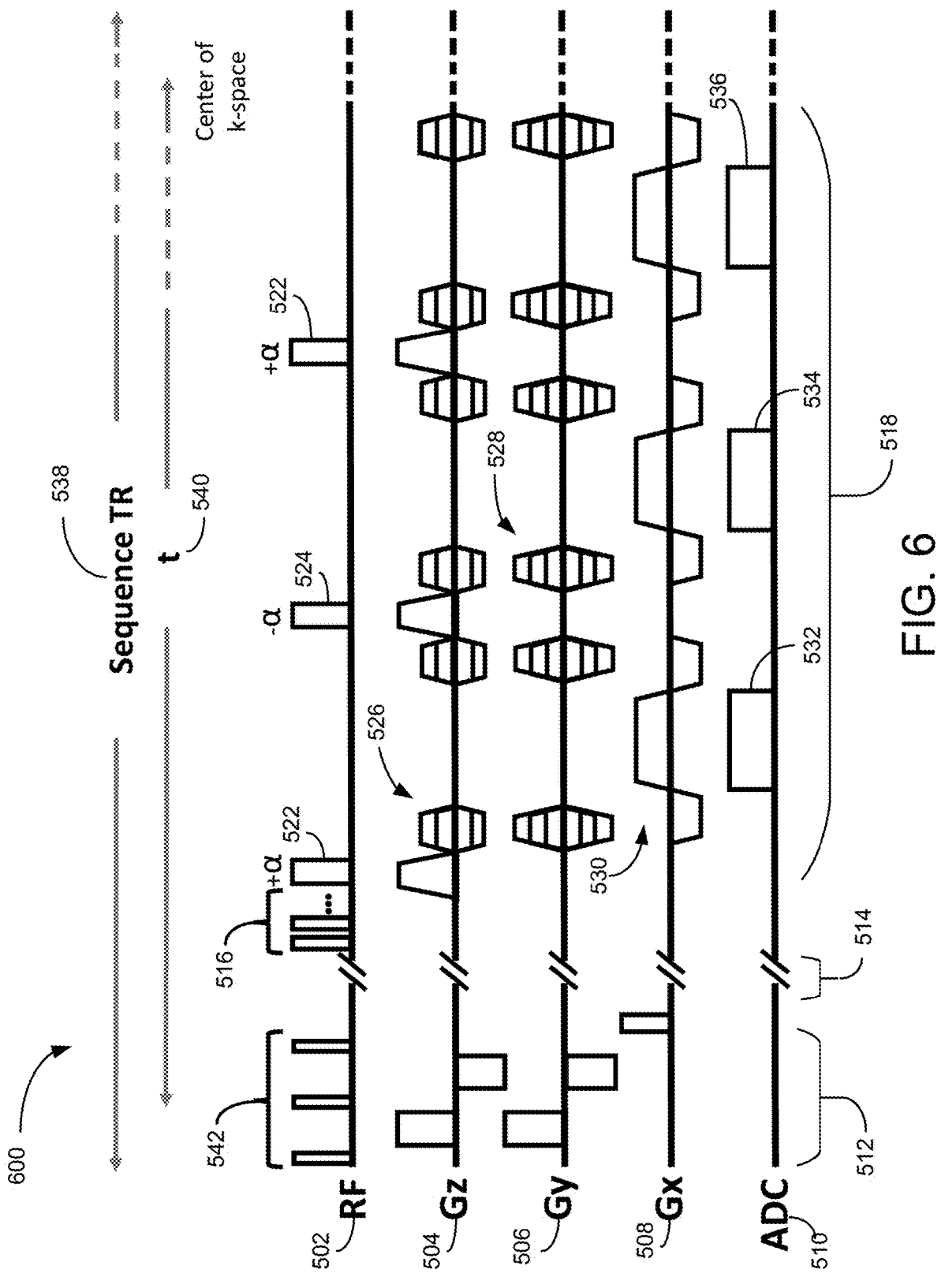
FIG. 6 is a pictorial representation of a balanced $T_1$ relaxation enhanced steady-state (bT$_1$RESS) pulse sequence for equilibrium phase contrast enhanced MR angiography in accordance with an embodiment.

FIG. 5 is a pictorial representation of a balanced $T_1$ relaxation enhanced steady-state ($bT_1RESS$) pulse sequence for equilibrium phase contrast enhanced MR angiography in accordance with an embodiment and FIG. 6 is a pictorial representation of a balanced $T_1$ relaxation enhanced steady-state ($bT_1RESS$) pulse sequence for equilibrium phase contrast enhanced MR angiography in accordance with an embodiment. Referring to FIGS. 5 and 6, the balanced $T_1RESS$ sequence 500, 600 provides the capability to perform equilibrium phase contrast-enhanced MRA using an extracellular contrast agent. In FIG. 5, axis 502 is the axis for radio frequency (RF) pulses, axis 504 is the slice-selection direction, axis 506 is the phase-encoding direction, axis 508 is the frequency encoding direction, and axis 510 is the generated signal (or echoes) illustrated as ADC. The sequence 500 includes a $T_1$-weighted magnetization preparation module 512, a waiting period 514, and a bSSFP readout 518. In some embodiments, the sequence 500 can also include one or more other preparation RF pulses 516 such as, for example, and $\alpha/2$ RF pulse or a fat saturation RF pulse. In some embodiments, the $T_1$-weighted magnetization preparation 512 can be implemented as a saturation recovery magnetization preparation. In some embodiments, the magnetization preparation 512 can include one or more CM RF pulses. In FIG. 5, a single CM RF pulse 520 is shown. In FIG. 6, the $bT_1RESS$ sequence 600 includes a composite saturation recovery module 542 that includes three CM RF pulses. Each CM RF pulse in the $T_1$-weighted magnetization preparation 512 has a flip angle ($CM\alpha$). In some embodiments, the flip angle $CM\alpha$ of the CM RF pulse(s) can be greater than or equal to 90°.

The waiting period 514 can be applied between the $T_1$-weighted magnetization preparation 512 and the single-shot bSSFP readout 518. As mentioned above, the waiting period can be a component of the time interval (t) 540 between the $T_1$-weighted magnetization preparation and the acquisition of a center of k-space which can be used to maximize contrast between the contrast-enhanced blood pool and another tissue. As mentioned, in some embodiments, the one or more other preparation RF pulses 516 can include an $\alpha/2$ RF pulse (where $\alpha$ is the imaging flip angle) that can be applied after the $T_1$ magnetization preparation 512, e.g., after CM RF pulse 520 or CM RF pulses 542, to drive the transverse magnetization towards the steady-state prior to application of $\pm\alpha$ excitation RF pulses 522, 524 in the bSSFP readout 518. In some embodiments, the one or more other preparation RF pulses 516 can include a plurality of dummy RF pulses to drive the transverse magnetization towards the steady-state prior to application of the $\pm\alpha$ excitation RF pulses 522, 524 in the bSSFP readout 518. In some embodiments, a fat saturation RF pulse may be applied prior to the single-shot bSSFP readout 518. In some embodiments, additional magnetization preparations such as, for example, a $T_2$ preparation, a magnetization transfer preparation, or a $T1_{rho}$ preparation may be applied before the bSSFP readout 518.

In some embodiments, SSFP readout 518 can be a single shot readout and can acquire all k-space data necessary for reconstructing an image during the sequence TR 538. The bSSFP readout 518 can include a plurality of excitation (or imaging pulses), illustrated as $\pm\alpha$ excitation RF pulses 522, 524 in FIGS. 5 and 6, and a plurality of echoes 532, 534, and 536. In some embodiments, the plurality of excitation RF pulses can have a flip angle larger than 45°. While three imaging echoes 532, 534, and 536 following the $\pm\alpha$ imaging RF pulses 522, 524 are shown in the bSSFP readout 518 in FIGS. 5 and 6, it should be understood that the $\pm\alpha$ excitation RF pulses 522, 524 can be repeatedly applied (followed by echoes) until all necessary k-space data are sampled in the bSSFP readout 518. In FIGS. 5 and 6, the bSSFP readout can also include slice-selection gradients 526 applied in the slice direction 504, phase encoding gradients 528 applied in the phase-encoding direction 508, and frequency encoding gradients 530 applied after excitation (or imaging) RF pulses 522, 524, illustrated as encoding direction 508. While one bT$_1$RESS sequence repetition time (TR) 538 for the sequence 500 is shown in FIGS. 5 and 6, it should be understood that the bT$_1$RESS sequence can be applied additional times. In some embodiments, for an application that requires more than one shot of the equilibrium phase bT$_1$RESS pulse sequence 500, the sequence repetition time TR 538 can be between 400 msec and 1600 msec.

As mentioned above, the bSSFP readout 518 is configured to collect MR data from the center of k-space (center k-space views) along a phase encoding direction during the equilibrium phase of contrast enhancement after completion of the first pass of the extracellular contrast agent through the region of interest. In other words, a first central phase encoding step can be acquired after the completion of the first pass of the extracellular contrast agent. Advantageously, as discussed above, the time interval 540 ($t$) between the $T_1$-weighted magnetization preparation pulse(s) and a center of k-space (or central view of k-space) along the phase encoding direction for an equilibrium phase bT$_1$RESS pulse sequence may be determined to enable the sequence 500, 600 to produce a diagnostic quality angiographic image during the equilibrium phase. In some embodiments, the bSSFP readout 518 can be cardiac gated (i.e., electrocardiographic (ECG)-gated), for example, using prospective gating. In some embodiments, the bSSFP readout 518 can be synchronized to a diastolic phase of the cardiac cycle, for example, to the quiescent phase of the cardiac cycle.

The equilibrium phase bT$_1$RESS technique described above with respect to FIGS. 4-6 can be combined with other imaging techniques. In one example, the disclosed equilibrium phase bT$_1$RESS technique can be used with image registration, motion compensation or respiratory gating methods. In another example, the disclosed equilibrium phase bT$_1$RESS technique can be used with partial Fourier imaging. In some embodiments, fat suppression may be obtained using SPAIR, Dixon multi-echo acquisition, or a radial fast interrupted steady-state technique. In another example, a pre-contrast mask image may be acquired for the purpose of image subtraction or other image manipulation. In another example, a maximum intensity projection or multi-planar reconstruction may be created from source images generated using the equilibrium phase bT$_1$RESS technique.

Computer-executable instructions for equilibrium phase contrast-enhanced MR angiography for a subject according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

I claim:

1. A method for equilibrium phase contrast-enhanced magnetic resonance (MR) angiography using an extracellular MR contrast agent administered to a subject, the method comprising:

performing, using a magnetic resonance imaging (MRI) system, a balanced $T_1$ relaxation enhanced steady-state pulse sequence to acquire MR data from a region of interest of the subject during an equilibrium phase of contrast enhancement after a first pass of the extracellular contrast agent through the region of interest, the balanced $T_1$ relaxation enhanced steady-state pulse sequence comprising:

a $T_1$-weighted magnetization preparation comprising at least one contrast modifying (CM) radio frequency (RF) pulse;

a single-shot balanced steady-state free precession (bSSFP) readout applied after the $T_1$-weighted magnetization preparation, the bSSFP readout comprising a plurality of excitation RF pulses and configured to acquire the MR data including a center of k-space in a plurality of echoes corresponding to the plurality of excitation RF pulses; and a time interval between the $T_1$-weighted magnetization preparation and the acquisition of the center of k-space, wherein the time interval is determined based on a $T_1$ relaxation time of a contrast-enhanced blood pool and a flip angle of the at least one CM RF pulse, and the time interval is configured to maximize a contrast between the contrast enhanced blood pool and at least one other tissue in the region of interest; and generating an angiographic image of the region of interest of the subject based on the acquired MR data, wherein blood vessels in the region of interest appear brighter than background tissues.

2. The method according to claim 1, wherein the $T_1$ relaxation time of the contrast-enhanced blood pool is one of an estimated $T_1$ relaxation time or a measured $T_1$ relaxation time.

3. The method according to claim 1, wherein the dose of the extracellular MR contrast agent administered to a subject is selected to at least double a $T_2/T_1$ ratio of the blood pool during the equilibrium phase of contrast enhancement.

4. The method according to claim 1, wherein the time interval is determined using:

$$t_{min} \approx T1_{blood\ pool} \times (CM\alpha/90)^{1/3}$$

where $T1_{blood\ pool}$ is the expected $T_1$ relaxation time of the blood pool during the equilibrium phase of contrast enhancement and $CM\alpha$ is the flip angle of the at least one CM RF pulse in the T1-weighted magnetization preparation.

5. The method according to claim 1, wherein the single shot bSSFP is synchronized to a quiescent phase of a cardiac cycle of the subject.

6. The method according to claim 1, wherein the balanced $T_1$ relaxation enhanced steady-state pulse sequence further comprises a plurality of dummy RF pulses applied after the $T_1$-weighted magnetization preparation and before the single shot bSSFP readout.

7. The method according to claim 1, wherein the balanced $T_1$ relaxation enhanced steady-state pulse sequence further comprises an $\alpha/2$ RF pulse applied after the $T_1$-weighted magnetization preparation and before the single shot bSSFP readout.

8. The method according to claim 1, wherein the time interval is between 100 msec and 600 msec.

9. The method according to claim 1, wherein the flip angle of the at least one contrast modifying (CM) radio frequency (RF) is greater than or equal to 90 degrees.

10. The method according to claim 1, wherein each of the plurality of excitation RF pulses has a flip angle larger than 45 degrees.

11. The method according to claim 1, wherein the balanced $T_1$ relaxation enhanced steady-state pulse sequence further comprises a fat saturation pulse applied after the $T_1$-weighted magnetization preparation and before the single shot bSSFP readout.

12. A magnetic resonance imaging (MRI) system comprising:

a magnet system configured to generate a polarizing magnetic field about at least a portion of a subject;

a plurality of gradient coils configured to apply at least one gradient field to the polarizing magnetic field;

a radio frequency (RF) system configured to apply an excitation field to the subject and to receive MR data from the subject; and a computer system programmed to:

direct the plurality of magnetic gradient coils and the RF system to perform a balanced $T_1$ relaxation enhanced steady-state pulse sequence to acquire MR data from a region of interest of the subject during an equilibrium phase of contrast enhancement after a first pass of the extracellular contrast agent through the region of interest, the balanced $T_1$ relaxation enhanced steady-state pulse sequence comprising:

a $T_1$-weighted magnetization preparation comprising at least one contrast modifying (CM) radio frequency (RF) pulse;

a single-shot balanced steady-state free precession (bSSFP) readout applied after the $T_1$-weighted magnetization preparation, the bSSFP readout comprising a plurality of excitation RF pulses and configured to acquire the MR data including a center of k-space in a plurality of echoes corresponding to the plurality of excitation RF pulses; and a time interval between the $T_1$-weighted magnetization preparation and the acquisition of the center of k-space, wherein the time interval is determined based on a $T_1$ relaxation time of a contrast-enhanced blood pool and a flip angle of the at least one CM RF pulse, and the time interval is configured to maximize a contrast between the contrast enhanced blood pool and at least one other tissue in the region of interest; and generate an angiographic image of the region of interest of the subject based on the acquired MR data, wherein blood vessels in the region of interest appear brighter than background tissues.

13. The MRI system according to claim 12, wherein the $T_1$ relaxation time of the contrast-enhanced blood pool is one of an estimated $T_1$ relaxation time or a measured $T_1$ relaxation time.

14. The MRI system according to claim 12, wherein the dose of the extracellular MR contrast agent administered to a subject is selected to at least double a $T_2/T_1$ ratio of the blood pool during the equilibrium phase of contrast enhancement.

15. The MRI system according to claim 12, wherein the time interval is determined using:

$$t_{min} \approx T1_{blood\ pool} \times (CM\alpha/90)^{1/3}$$

where $T1_{blood\ pool}$ is the expected $T_1$ relaxation time of the blood pool during the equilibrium phase of contrast enhancement and $CM\alpha$ is the flip angle of the at least one CM RF pulse in the T1-weighted magnetization preparation.

16. The MRI system according to claim 12, wherein the single shot bSSFP is synchronized to a quiescent phase of a cardiac cycle of the subject.

17. The MRI system according to claim 12, wherein the balanced $T_1$ relaxation enhanced steady-state pulse sequence further comprises a plurality of dummy RF pulses applied after the $T_1$-weighted magnetization preparation and before the single shot bSSFP readout.

18. The MRI system according to claim 12, wherein the balanced $T_1$ relaxation enhanced steady-state pulse sequence further comprises an $\alpha/2$ RF pulse applied after the $T_1$-weighted magnetization preparation and before the single shot bSSFP readout.

19. The MRI system according to claim 12, wherein the time interval is between 100 msec and 600 msec.

20. The MRI system according to claim 12, wherein the flip angle of the at least one contrast modifying (CM) radio frequency (RF) is greater than or equal to 90 degrees.

21. The MRI system according to claim 12, wherein each of the plurality of excitation RF pulses has a flip angle larger than 45 degrees.

22. The MRI system according to claim 12, wherein the balanced $T_1$ relaxation enhanced steady-state pulse sequence further comprises a fat saturation pulse applied after the $T_1$-weighted magnetization preparation and before the single shot bSSFP readout.

\* \* \* \* \*